United States Patent

Bekki et al.

Patent Number: 5,246,462
Date of Patent: Sep. 21, 1993

[54] INSERT FOR IDENTIFYING AN IMPLANTABLE CERAMIC JOINT HEAD

[75] Inventors: Katsutoshi Bekki; Jun Sugimoto, both of Aichi, Japan

[73] Assignee: NGK Spark Plug Co., Ltd., Aichi, Japan

[21] Appl. No.: 926,399

[22] Filed: Aug. 10, 1992

[30] Foreign Application Priority Data

Aug. 13, 1991 [JP] Japan .................. 3-072095[U]

[51] Int. Cl.$^5$ .................................. A61F 2/36
[52] U.S. Cl. .................................. 623/23
[58] Field of Search ........... 623/11, 16, 18, 20, 623/22, 23, 66

[56] References Cited

U.S. PATENT DOCUMENTS

| | | | |
|---|---|---|---|
| 4,202,349 | 5/1980 | Jones | 128/899 |
| 4,233,964 | 11/1980 | Jefferts et al. | 128/899 |
| 4,685,919 | 8/1987 | Niwa et al. | 623/16 |
| 4,863,470 | 9/1989 | Carter | 623/8 |
| 4,923,471 | 5/1990 | Morgan | 623/16 |
| 4,944,758 | 7/1990 | Bekki et al. | 623/16 |
| 4,988,338 | 1/1991 | Taylor et al. | 604/180 |
| 5,007,932 | 4/1991 | Bekki et al. | 623/16 |
| 5,092,898 | 3/1992 | Bekki et al. | 623/16 |

FOREIGN PATENT DOCUMENTS 0011665  6/1980  European Pat. Off. ........... 623/22

Primary Examiner—David Isabella
Attorney, Agent, or Firm—Finnegan, Henderson, Farabow, Garrett & Dunner

[57] ABSTRACT

An object of this invention is to provide an implantable ceramic joint head which can be readily marked without a reduction in the strength of the ceramic. In the artificial ceramic joint head of the present invention having a recess into which a stem is inserted, an insert with a marking is provided in the bottom of the recess.

3 Claims, 1 Drawing Sheet

INSERT FOR IDENTIFYING AN IMPLANTABLE CERAMIC JOINT HEAD

BACKGROUND OF THE INVENTION

This invention relates to an implantable joint head which is used to replace the head of the femur of the human body which has been damaged by fracture or malum coaxe deformans.

When an implantable joint head of this type is put on the market, it is necessary to provide its historical data, such as, marking it with a manufacture number. This marking will be described with reference to FIG. 4. In a conventional marking method, after an implantable joint head 1 of ceramic is sintered, numerical data or the like is engraved with an edged tool on the end face 2, in which a recess is opened, or on the outer spherical surface 3. Thereafter, a metal stem (not shown) is fixedly inserted into the recess 4 to complete the manufacture of the implantable joint head.

In another method, after an implantable joint head is sintered, a manufacture number or the like is marked on it with a laser or ultrasonic marking machine, and then a metal stem is fixed into the recess.

As described above, in the conventional marking method, the surface of the implantable joint head is scratched by the marking method. In other words, a number of defects, namely, scratches, are formed in the surface. In this connection, a static load strength test revealed that an implantable joint head with an engraved end face has about a 25% lower mechanical strength than one which is not engraved.

Furthermore, it is rather difficult to put a marking on the narrow surface of the end face according to the conventional marking method.

SUMMARY OF THE INVENTION

An object of this invention is to eliminate the above-described difficulties accompanying a conventional implantable ceramic joint head. More specifically, an object of the invention is to provide an implantable ceramic joint head which can be readily marked without reduction in the mechanical strength of the ceramic.

The foregoing object of the invention has been achieved by the provision of an implantable ceramic joint head having a recess formed therein, in which, according to the invention, an insert having an identifying marking is disposed at the end of the recess.

The insert is preferably in the form of a disc; however, it may be polygonal. The insert may be made of resin or metal. In the case of a resin insert, it is preferable to use high density polyethylene; however, "Teflon" or polyacetal may be employed. In the case of a metal insert, it is preferable to use titanium; however, stainless steel or cobalt chromium alloy may be employed. At any rate, the insert should be made of a material which is high in corrosion resistance and not poisonous. The disc is formed as follows: disc 0.1 to 2 mm in thickness is prepared with a diameter that is larger than the diameter of the bottom of the recess in the joint head by 0.2 to 2 mm. Cuts are formed in the peripheral portion of the disc, or through-holes are formed in the disc, so as to allow the flow of sterilizing gas when sterilizing the joint head. A marking, such as a manufacture number, is put on the disc by engraving it.

The disc thus marked is inserted into the recess of the joint head and fixedly held in the recess at the bottom.

As was described above, the disc is larger by about 1 mm in diameter than the diameter of the bottom of the recess. Therefore, when the disc is forcibly pushed into the bottom of the recess, the edges of the disc are curved away from the direction of insertion because of the disc's larger diameter. As a result, the disc is fixedly held in the recess in such a manner that it is in contact with the wall of the recess and is spaced a distance from the bottom of the recess.

The implantable ceramic joint head of the invention is manufactured separately from its mating stem. The stem has a protrusion, which is fixedly inserted into the recess of the joint head. For this purpose, the protrusion of the stem is tapered, and the recess of the joint head is also tapered. In the case where the stem is connected to the joint head in this manner, high accuracy is essential in machining the recess to form a tapered wall. Machining in the form of grinding can provide this high accuracy. When grinding, a grinding clearance groove is necessary in the recess. That is, in the joint head of the invention, a clearance groove is formed in the bottom of the recess. This clearance groove may also be utilized to hold the marked insert.

In the invention, the marking is not directly put on the implantable joint head and, therefore, the ceramic is not reduced in mechanical strength. Further, the insert can be marked before it is inserted into the joint head. Hence, the whole area of the insert can be used for marking; that is, the marking operation can be more easily performed.

The marked insert is held inside the joint head; that is, the insert is safely held therein until the joint head is broken. Even if the joint head is broken, the marked insert will never be damaged to the extent that the marking scratched directly on the joint would be damaged because the marking insert is held a distance spaced from the bottom of the recess. Thus, the historical data can be confirmed at all times.

DETAILED DESCRIPTION OF THE PREFERRED EMBODIMENT

Figure 1A:
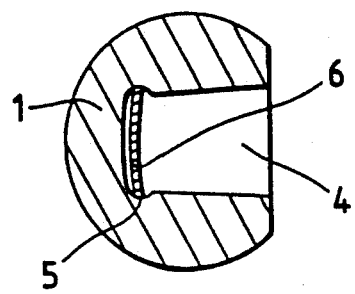
FIG. 1(A) is a vertical sectional view of an implantable ceramic joint head into which an insert is fixedly inserted.
Figure 1B:
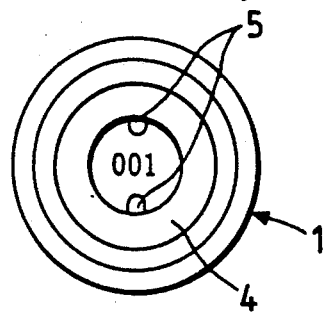
FIG. 1(B) is a right side view of the implantable ceramic joint head as viewed from the right side in FIG. 1(A)
Figure 2A:
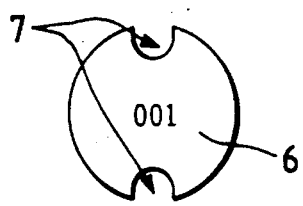
FIGS. 2(A) and (B) are plan views showing examples of the insert.
Figure 2B:
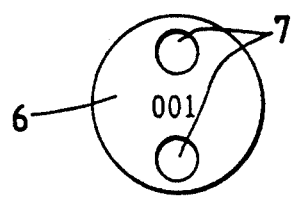

FIG. 1(A) is a cross sectional view of an implantable ceramic joint head 1 into which an insert is fixedly seated, and FIG. 1(B) is a side view showing the implantable ceramic joint head as viewed from the right side of FIG. 1(A). FIGS. 2(A) and 2(B) are plan views showing examples of the insert. Each of the inserts is in the form of a disc and has a manufacture number engraved on one side. The seat shown in FIG. 2(A) has two elongated cuts in the periphery that allow the passage of gas during sterilization, and the disc shown in FIG. 2(B) has two circular through-holes in it for the same purpose.

Figure 3:
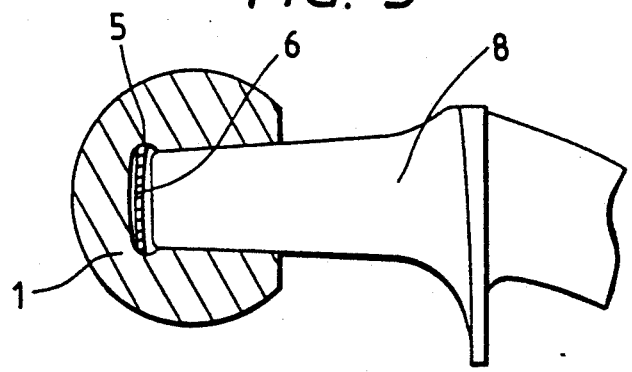
FIG. 3 is a sectional view of the implantable ceramic joint head in which the insert is seated and then a stem is inserted, substantially showing the insert's actual use.
Figure 4A:
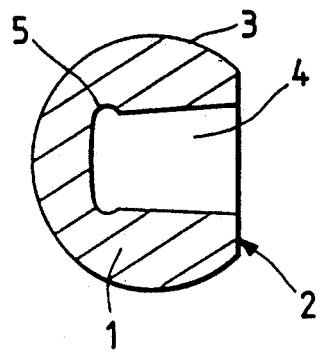
FIG. 4(A) is a vertical sectional view of an implantable ceramic joint head which is marked by a conventional marking method.
Figure 4B:
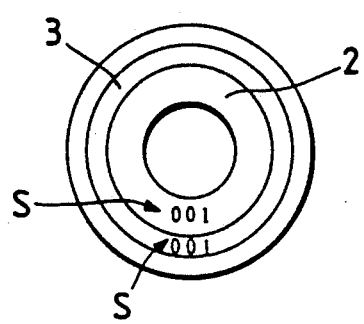
FIG. 4(B) is a right side view of the implantable ceramic joint head.

FIG. 3 is a sectional view of the implantable ceramic joint head in which the insert 6 is seated and a stem is then inserted, substantially showing the insert's actual use.

In FIG. 1(A), the artificial joint head 1 is made of ceramic, such as alumina, zirconia or calcium phosphate. The artificial joint head 1 is substantially in the form of a sphere about 22 to 32 mm in diameter, and has a cylindrical recess 4 on one side, the bottom of the recess being located near the center of the artificial joint head. The recess 4 has an outer circular edge 10 to 12 mm in diameter and is tapered toward the bottom to a diameter that is 1 mm smaller than the outer circular edge. Thereafter, the diameter is increased by 0.5 to 2 mm to form a clearance groove 5 used for machining the inner wall of the recess 4.

The insert 6 is a disc of high-density polyethylene that has a diameter that is about 1 mm larger than the diameter of the clearance groove 5. In FIG. 2(A), the insert 6 has two elongated cuts 7 in the peripheral portion through which sterilizing gas is allowed to flow. The seat 6 has an engraved manufacture number or the like on its one side. The insert 6 is inserted into the clearance groove 5 while being elastically deformed. In this operation, the elastic force of the insert 6 acts on the annular wall of the clearance groove 5 to fixedly secure the insert 6 therein.

By way of example, the implantable ceramic joint head 1 is manufactured by the following steps. Before sintering, the spherical ceramic body 1 is drilled to form recess 4. The spherical ceramic body 1 with the recess 4 is sintered, and the inner wall of the recess 4 is ground with a grinding stone. In this grinding operation, the clearance groove 5 makes it possible to apply the grinding stone on all of the tapered inner wall of the recess 4. Thereafter, insert 6 is forcibly inserted into the recess 4 so that it is brought into contact with the annular wall of the clearance groove 5. The insert 6, with the edges curved, is fixedly secured in the clearance groove 5 by elastic force. Under this condition, the implantable joint head 1 with the insert 6 is sterilized by using sterilizing gas, and the tapered protrusion of the stem 8 is fixedly inserted into the tapered recess 4 as shown in FIG. 3. There is a clearance about 2 mm between the bottom of the recess 4 and the end of the tapered protrusion of the stem 8; thus, the insert 6 is not collapsed by the stem 8.

What is claimed is:

1. An implantable artificial ceramic joint head to replace a natural joint head of a body comprising:
   a ceramic body having a recess formed therein, said recess having an inner wall defining an outer circular edge and an inner blind bore tapering to an end wall opposite said outer circular edge; and
   a separate disc having an identifying marking wherein said disc is disposed in said recess adjacent said end wall.

2. An implantable ceramic joint head as claimed in claim 1, wherein said recess further comprising an enlarged clearance defined between said inner wall and said end wall.

3. An implantable ceramic joint head as claimed in claim 2, wherein said disc has a diameter greater than said enlarged clearance.

* * * * *